United States Patent [19]

Dougherty

[11] 3,985,814

[45] Oct. 12, 1976

[54] PRODUCTION OF ALCOHOLS FROM CARBOXYLIC ACIDS

[75] Inventor: Edward F. Dougherty, Corpus Christi, Tex.

[73] Assignee: Celanese Corporation, New York, N.Y.

[22] Filed: Feb. 28, 1975

[21] Appl. No.: 554,251

[52] U.S. Cl. .............................. 260/635 D; 260/575; 260/584 R; 260/618 H; 260/633; 260/638 A
[51] Int. Cl.$^2$ .......................................... C07C 29/00
[58] Field of Search......... 260/638 A, 635 D, 638 A

[56] References Cited
UNITED STATES PATENTS

| | | | |
|---|---|---|---|
| 2,064,493 | 7/1952 | Copenhaver................... | 260/638 A |
| 2,080,419 | 5/1937 | Green............................ | 260/638 A |
| 2,456,633 | 12/1948 | Haensel......................... | 260/638 A |
| 3,125,605 | 5/1964 | Buchner et al. ............... | 260/638 A |
| 3,268,588 | 8/1966 | Horlenko et al............... | 260/635 D |
| 3,478,103 | 11/1969 | Hann............................. | 260/635 D |
| 3,736,265 | 5/1973 | Suggit............................ | 260/638 A |

Primary Examiner—Joseph E. Evans

[57] ABSTRACT

A process for the conversion of carboxyl groups to methylol groups by hydrogenolysis utilizing a platinum catalyst.

7 Claims, No Drawings

PRODUCTION OF ALCOHOLS FROM CARBOXYLIC ACIDS

BACKGROUND OF THE INVENTION

The present invention relates to a method whereby the carboxyl groups on an organic compound may be converted to methylol groups, for example, a method of converting adipic acid to 1,6-hexanediol. In various industrial processes it is necessary to convert a compound containing a carboxyl group to the corresponding primary alcohol; however, at the present time no really efficient processes have been developed for accomplishing such. For example, in the production of 1,6-hexanediol from adipic acid, the most popular method for accomplishing such is to first esterify the adipic acid with an alcohol and then hydrogenolyze the ester to obtain a product comprising 1,6-hexanediol and the alcohol utilized in the esterification. Obviously, a direct route from the acid to the alcohol would be more desirable than one involving the formation of an intermediate. Processes have been developed whereby a carboxyl compound may be converted to the corresponding hydroxyl compound but such processes have been found to be substantially inefficient and uneconomical because of low conversions and other process problems. Examples of prior art include U.S. Pat. No. 3,344,196 issued Sept. 26, 1967 to Hubert Corr, et al., and the article by H. Smith Broadbent, et al., "Rhenium and its Compounds as Hydrogenation Catalysts. III. Rhenium Heptoxide," Journal of Organic Chemistry, Vol. 24, P. 1847 (1959).

It is thus an object of the present invention to provide a process whereby an organic compound containing carboxyl groups may be efficiently processed to convert such groups directly to methylol ($-CH_3OH$) groups without the necessity of the formation of any intermediates. It is a particular object of the present invention to provide a process whereby alkanoic monocarboxylic and dicarboxylic acids may be converted directly to the corresponding alcohols or diols with good efficiency. Additional objects will become apparent from the following description of the present invention.

SUMMARY

These and other objects are accomplished by the present invention which in one of its aspects is a process comprising reacting a first organic compound containing one or more carboxyl groups, each of which is attached to a carbon atom not a part of a carboxyl group, with molecular hydrogen in the presence of a metallic platinum catalyst under hydrogenolysis conditions, wherein the temperature is within the range of 100° to 325° C and the pressure is sufficient to maintain a liquid phase of said first organic compound and is within the range of 70 to 700 atmospheres absolute, for a sufficient period of time to convert at least a portion of said carboxyl groups to methylol groups; and, separating from the reaction product a second organic compound containing said methylol groups, the carbon skeleton of said second organic compound being the same as that of said first organic compound.

DETAILED DESCRIPTION OF THE INVENTION

The present invention may be utilized to convert a carboxyl group on practically any organic compound to a methylol group by hydrogenolysis. The resulting organic compound product will have the same carbon skeleton as the starting carboxylated compound. In many instances, the hydroxylated product will in fact be identical to the carboxylated starting compound except that methylol groups will exist where carboxyl groups existed on the starting compound. The carboxyl group must be attached to a carbon atom which is not a part of a carboxyl group so as to obtain the desired results. Thus a monocarboxylic compound must contain at least two carbon atoms, a dicarboxylic acid must contain at least three carbon atoms and the like in order to satisfy such criteria. Compounds such as formic acid and oxalic acid may thus not be converted, respectively, to methanol and ethylene glycol by the present invention.

In some instances, the hydrogenolysis will affect not only the carboxyl groups but will also affect sites other than the carboxyl groups such that the product differs from the starting compound in ways other than the mere conversion of carboxyl groups to methylol groups. In these latter instances, the carbon skeleton will, however, be unaffected. For example, if the carboxylated compound being hydrogenolyzed contains ethylenic or acetylenic unsaturation, saturation of the unsaturated linkages will occur. Similarly, if the carboxyl compound contains a secondary hydroxyl group, the hydrogenolysis will effect the replacement of the secondary hydroxyl group with a hydrogen atom. Thus, if 3-hydroxybutanoic acid is hydrogenolyzed according to the present invention, the product will be 1-butanol, and 2-hydroxyhexanoic acid will be converted to 1-hexanol. It is generally preferred that the carboxyl-containing organic compound being hydrogenolyzed be a substituted or unsubstituted hydrocarbon compound of 2 to 30 carbon atoms containing in addition to the carboxyl groups no substituents other than hydroxyl, halogen, nitro and amino, especially such compounds that are acyclic in nature. The alkanoic monocarboxylic and dicarboxylic acids are especially suitable for the present invention with best results being obtained with those alkanoic monocarboxylic acids containing from 2 to 7 carbon atoms and those alkanoic dicarboxylic acids containing from 3 to 7 carbon atoms. The invention is most beneficial in the conversion of adipic acid or 6-hydroxyhexanoic acid or mixtures thereof to 1,6-hexanediol.

Specific organic compounds that may be hydrogenolyzed according to the invention include 2-bromocaproic acid, 6-hydroxyhexanoic acid, adipic acid, succinic acid, acetic acid, butanoic acid, glutaric acid, vinylacetic acid, orthotoluic acid, para amino-alpha toluic acid, tartaric acid, tridecanoic acid, palmitic acid, stearic acid and linoleic acid.

The hydrogenolysis of the present invention is a liquid phase reaction, that is the carboxylated compound to be hydrogenolyzed must be in the liquid phase although the hydrogen itself will be in the gas phase. In order to obtain a liquid phase of many of the various carboxylated compounds it will be necessary to utilize an inert solvent medium because the carboxylated compounds are solids under the reaction conditions. The solvent medium utilized may be any which is substantially inert under the reaction conditions in the reaction zone. By "substantially inert" is meant that the solvent does not react with itself or with the other components present in the reaction zone (including reactants and products) to a substantial extent, and, does not otherwise interfere or hinder the desired hydrogenolysis reaction. The solvent does not have to be totally inert since even the preferred solvent, water, will react somewhat with various of the components present in the reaction zone. Generally recommended as a solvent medium is water, an ether, an alcohol, or mixtures thereof. Ethers that may be used include the cyclic and acyclic ethers. Preferred are the alkyl or cycloalkyl ethers and the alkyl or cycloalkyl alcohols. Specific suitable solvents in addition to water are diethyl ether, ethylbutyl ether, methanol, ethanol, hexanol, 1,4-dioxane, tetrahydrofuran, and petroleum ether. The carboxylated compound may be dissolved in a solvent prior to the hydrogenolysis or a solution of the carboxylated compound which is the by-product of another process may be utilized. The concentration of the carboxylated compound in solution may vary widely and may be up to solubility limits.

To carry out the process, the carboxylated compound in the liquid phase (which as pointed out above may be a solution of the carboxylated compound) is contacted with hydrogen while also in contact with the platinum catalyst. The liquid and the gaseous hydrogen may be led over a fixed bed of the catalyst or the catalyst may be slurried in the liquid and the resulting slurry contacted with the hydrogen. The hydrogen itself may be led concurrently or countercurrently. As a general rule, technically pure hydrogen will be utilized but it is also possible to use gases rich in hydrogen, such as coke, oven gas, water gas or town gas.

The hydrogenolysis reaction needs to be carried out at elevated temperatures and elevated pressures sufficient to cause the desired conversion of carboxyl groups to methylol groups, and, of course, the pressure must be sufficient to maintain a liquid phase of the carboxylated compound (which may be a solution thereof). Generally, temperatures within the range of 100° to 325° C may be used, the preferable range being from about 175° to 250° C. Superatmospheric pressures are necessary, those within the range of about 70 to 700 atmospheres absolute being generally utilized, with preferred ranges being about 140 to 400 atmospheres absolute. The contact time or residence time may vary widely with good conversions being realized under some conditions after about 0.5 hour or less, with usual residence times being about 0.5 to 4.0 hours. In a fixed bed process, the flow rate of liquid feed may vary widely, for example, from about 100 to 2,000 milliliters per hour per liter of catalyst. Obviously, the concentration, temperature, pressure and catalyst composition will greatly affect such. Thus, the foregoing range is not to be taken as limiting the scope of the present invention.

The catalyst used in the process is a metallic catalyst of platinum. The method of making the catalyst does not comprise a part of the present invention as metallic platinum catalysts are well known and are generally commercially available. The main requirement is that the catalyst have a surface containing the metallic platinum. The metallic platinum catalyst may be prepared in situ such as by reduction of a metal salt in the hydrogenolysis reactor under reaction conditions or by an ex situ reduction prior to the hydrogenolysis. Metal salts or compounds that may be reduced include oxides, sulfides and the like. A platinum gauze has been found sufficient as has platinum black. The reason for stating that a catalyst has a catalytically active surface comprised of the metallic platinum is that it is not known whether reduction of a metal oxide or the like serves to reduce all of the oxide or merely that on the surface. In a solid catalyst it is generally the surface of a catalyst particle which is effective as a catalyst and not the interior of the particle.

The metallic platinum catalyst may be supported on carrier substances such as pumice, alumina, kieselguhr, silica gel, synthetic silicates, porcelain, quartz, and the like. The size and shape of the catalyst particles are not critical. For example, the catalysts may be in the form of pellets, powder, pills, spheres, etc. Also reactor size has no bearing on the operation of the invention but it is presumed that the optimum size to give the proper residence time is used. Reactors of conventional configuration may be used.

The methylol group-containing product may be readily separated from the reactor effluent by standard distillation techniques. Generally, a series of three distillation towers will affect a good separation, with the light ends and solvents removed as overheads from the first tower. The residue of the first tower would be passed to the second tower where the unreacted acids and heavy ends would be removed as residue and a crude product recovered as overheads. The third tower would be a finishing tower. Of course, for efficient operation the unreacted acids and solvent so recovered would be recycled to the hydrogenation reactor.

EXAMPLE

A hydrogenation reduction system was employed which comprised a two-liter stainless steel rocking autoclave, provided with means for measuring and controlling the internal temperature and hydrogen pressure. The autoclave was charged with 100 grams of 5% platinum on carbon. The reactor was next charged with 0.5 liter of an aqueous solution of an acid fraction separated from the reaction product of a cyclohexane oxidation wherein cyclohexane had been oxidized to produce a non-acid fraction comprising cyclohexanone and cyclohexanol and an acid fraction comprising mainly adipic acid but also containing amounts of 6-hydroxyhexanoic acid, glutaric acid, succinic acid, and various alkanoic monocarboxylic acid. The particular aqueous solution placed in the autoclave contained, by weight, about 17% adipic acid, 13% 6-hydroxyhexanoic acid, 3.5% glutaric acid, 1.5% succinic acid, 25%, $C_1$ to $C_6$ alkanoic monocarboxylic acids, and 40% water. A hydrogen atmosphere at approximately 300 atmospheres absolute pressure was applied, the internal temperature was adjusted to approximately 265° C, and the reactor was agitated by rocking under these conditions for approximately four hours. At the end of this period, the reactor was allowed to cool, the hydrogen atmosphere was released, and product solution was analyzed. Analysis showed that about 95% of the various dicarboxylic and monocarboxylic acids had been converted, respectively, to the corresponding alkanediols (e.g. adipic to 1,6-hexanediol) and monohydric alkanols (e.g. acetic to ethanol) except for the formic acid present which was converted to carbon dioxide. The 6-hydroxyhexanoic acid was, like the adipic acid, converted to 1,6-hexanediol.

The embodiments of the invention in which an exclusive property or privilege is claimed are defined as follows:

1. A process for converting a feed comprising an acyclic monocarboxylic acid having 2 to 7 carbon atoms or a dicarboxylic acid having 3 to 7 carbon atoms or mixture thereof to the corresponding methylol-substituted compound in which the carboxyl groups in said feed are replaced by methylol groups, which process comprises:

reacting said acid, in aqueous solution and in the presence of a metallic platinum catalyst, at a temperature with the range of 100° C to 325° C and a pressure within the range of 70 to 700 atmospheres sufficient to maintain a liquid phase, for a period of time sufficient to convert at least a portion of said the carboxyl groups in said feed to methylol groups, said acid being free of substituents other than hydroxyl.

2. The process of claim 1 wherein the dicarboxylic acid is a dicarboxyalkane.

3. The process of claim 2 wherein the reaction is conducted at a temperature of about 175° to 250° C and at a pressure of about 140 to 400 atmospheres.

4. The process of claim 3 wherein the reaction time is from about 0.5 to 4.0 hours.

5. The process of claim 2 wherein the dicarboxylic acid is adipic acid and the methylol-substituted compound is 1,6-hexanediol.

6. The process of claim 1 wherein said feed comprises adipic acid or 6-hydroxyhexanoic acid or mixtures thereof, and said methylol-substituted compound is 1,6-hexanediol.

7. The process of claim 1 wherein said feed is an acid fraction separated from the reaction product of a cyclohexane oxidation.

* * * * *